United States Patent
Katzer

(10) Patent No.: US 9,908,973 B2
(45) Date of Patent: Mar. 6, 2018

(54) ADDITIVE FOR POLYAMIDE MOULDING COMPOUNDS AND USE THEREOF

(71) Applicant: UHDE INVENTA-FISCHER GMBH, Berlin (DE)

(72) Inventor: Johannes Katzer, Berlin (DE)

(73) Assignee: UHDE INVENTA-FISCHER GmbH, Berlin (DE)

(*) Notice: Subject to any disclaimer, the term of this patent is extended or adjusted under 35 U.S.C. 154(b) by 13 days.

(21) Appl. No.: 14/763,086

(22) PCT Filed: Jan. 23, 2014

(86) PCT No.: PCT/EP2014/051343
§ 371 (c)(1),
(2) Date: Jul. 23, 2015

(87) PCT Pub. No.: WO2014/114721
PCT Pub. Date: Jul. 31, 2014

(65) Prior Publication Data
US 2015/0329671 A1 Nov. 19, 2015

(30) Foreign Application Priority Data
Jan. 25, 2013 (EP) ...................................... 13152696

(51) Int. Cl.
C08G 69/26 (2006.01)
C07D 211/58 (2006.01)

(52) U.S. Cl.
CPC ............ *C08G 69/26* (2013.01); *C07D 211/58* (2013.01)

(58) Field of Classification Search
None
See application file for complete search history.

(56) References Cited

U.S. PATENT DOCUMENTS 4,102,870 A 7/1978 Hofmann et al.
4,145,512 A 3/1979 Uhrhan et al.
(Continued)

FOREIGN PATENT DOCUMENTS

DE 27 19 132 A1 12/1977
DE 198 04 980 A1 8/1999
(Continued)

OTHER PUBLICATIONS

La Mantia et al., "Thermo- and photo-oxidative stability and improved processability of polyamide stabilized with a new functional additive," *Polymers for Advanced Technologies 16*, pp. 357-361 (2005).
(Continued)

*Primary Examiner* — Rachel Kahn
(74) *Attorney, Agent, or Firm* — Leydig, Voit & Mayer, Ltd.

(57) ABSTRACT

The invention relates to an additive having at least two functionalities being able to undergo a condensation reaction in combination with a tetraalkylpiperidinyl radical and also a tertiary amine functionality. By the combination of these functionalities, a universal additive can be provided, which, on the one hand, makes possible a narrower molar mass distribution and, at the same time, improves the performance for spun polymers. According to the invention, likewise corresponding additivated polyamide molding compounds and also an additive solution are provided. The additives according to the invention are used in particular in the production of polyamide for textile applications.

6 Claims, 2 Drawing Sheets

(56) References Cited

U.S. PATENT DOCUMENTS

| | | | |
|---|---|---|---|
| 4,578,472 A * | 3/1986 | Yoshimura | C08K 5/3435 252/403 |
| 5,112,979 A | 5/1992 | Lin et al. | |
| 5,917,004 A | 6/1999 | Liedloff | |
| 5,955,558 A | 9/1999 | Gras et al. | |
| 6,204,351 B1 | 3/2001 | Gras et al. | |
| 6,423,817 B1 | 7/2002 | Weinerth et al. | |
| 6,812,323 B1 | 11/2004 | Breiner et al. | |
| 2002/0169181 A1 | 11/2002 | Pairet et al. | |

FOREIGN PATENT DOCUMENTS

| | | |
|---|---|---|
| DE | 198 12 135 A1 | 9/1999 |
| DE | 10200802607 A1 | 12/2009 |
| EP | 0 047 967 A1 | 3/1982 |
| EP | 0 488 502 A1 | 6/1992 |
| EP | 0 759 953 B1 | 3/1997 |
| EP | 0 818 491 A2 | 1/1998 |
| EP | 0 839 854 A1 | 5/1998 |
| JP | S53-039396 A | 4/1978 |
| JP | S57-080453 A | 5/1982 |
| JP | S59-219346 A | 12/1984 |
| JP | H05-017444 A | 1/1993 |
| JP | H10-139851 A | 5/1998 |
| WO | WO 1997/05189 A1 | 2/1997 |

OTHER PUBLICATIONS

Raje et al., "Molecular Weight Distribution and its Impact on Melt Spinning of Synthetic Polymers Part-II," *Man-Made Textiles in India*, pp. 173-178 (1996).

Tang et al., "Simulation of the hydrolytic polymerization of ε-caprolactam with bifunctional regulators," *Die Angewandte Makromolekulare Chemie 250*: pp. 1-14 (1997).

European Patent Office, International Search Report in International Application No. PCT/EP2014/051343 (dated Feb. 20, 2014).

European Patent Office, Written Opinion in International Application No. PCT/EP2014/051343 (dated Feb. 20, 2014).

International Bureau of WIPO, International Preliminary Report on Patentability in International Application No. PCT/EP2014/051343 (dated Jul. 28, 2015).

Japan Patent Office, Notification of Reasons for Rejection in Japanese Patent Application No. 2015-554146 (dated Oct. 3, 2017).

* cited by examiner

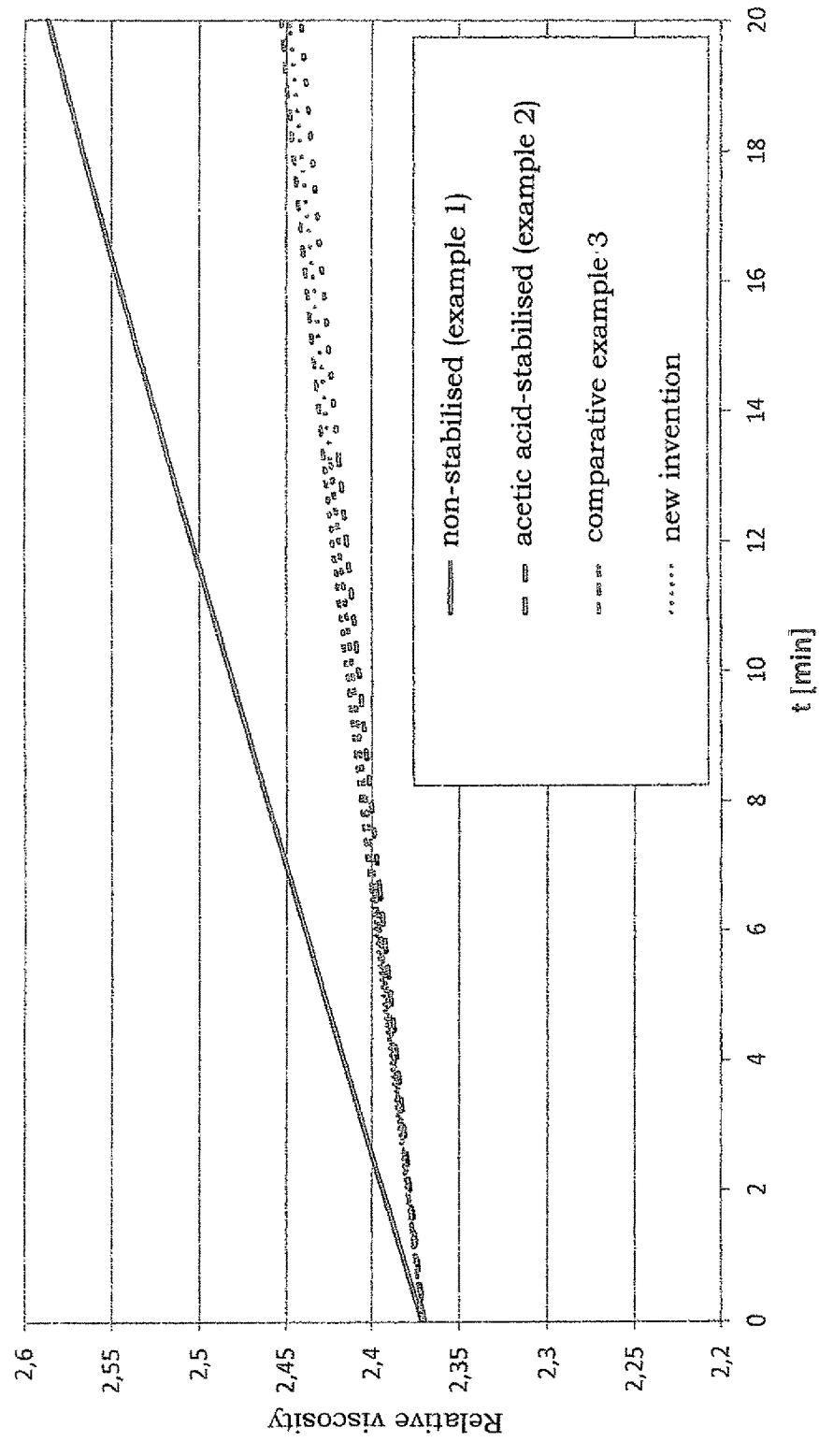

ADDITIVE FOR POLYAMIDE MOULDING COMPOUNDS AND USE THEREOF

CROSS-REFERENCE TO RELATED APPLICATIONS

This patent application is the U.S. national phase of International Application No. PCT/EP2014/051343, filed on Jan. 23, 2014, which claims the benefit of European Patent Application No. 13152696.4, filed Jan. 25, 2013, the disclosures of which are incorporated herein by reference in their entireties for all purposes.

The invention relates to an additive having at least two functionalities being able to undergo a condensation reaction in combination with a tetraalkylpiperidinyl radical and also a tertiary amine functionality. By the combination of these functionalities, a universal additive can be provided, which, on the one hand, makes possible a narrower molar mass distribution and, at the same time, improves the performance for spun polymers. According to the invention, likewise corresponding additivated polyamide moulding compounds and also an additive solution are provided. The additives according to the invention are used in particular in the production of polyamide for textile applications.

There is a series of requirements for the use of polyamide for textile application which these systems must fulfil:
- With the constantly increasing throughputs in spinning mills (high-speed spinning), also the requirements on the polymer have increased. Good spinnability with low thread breakage rates is expected.
- In order that the produced threads maintain their mechanical and optical properties for as long as possible, resistance to air oxygen and natural weathering conditions is desired.
- In order that the polymer changes its physical properties as little as possible during remelting and during the spinning process, high melt stability is required (low monomer reformation and low postcondensation).
- The threads must be readily dyeable.
- Additives for achieving the desired performance must be obtainable and applicable with an economic cost-benefit ratio.

For good spinnability, in particular at high draw-off speeds, the use of multifunctional stabilisers has proved its worth, which stabilisers have a narrowing influence on the molar mass distribution. Above all, multifunctional carboxylic acids are used, which, at the same time, keep low the content of primary amine groups in the condensation equilibrium and hence are favourable for a low monomer reformation during remelting. By way of example for the use of multifunctional acids as additives for the polyamide production, EP 0 818 491 A1 and EP 0 759 953 A1 may be mentioned. The narrowing influence on the molar mass distribution can be deduced, for example from the technical article by Z.-L. Tang et al. which appeared in "Die Angewandte Makromolekulare Chemie" (Applied Macromolecular Chemistry) (250, 1-14, No. 4321, 1997). The fact that a narrower molar mass distribution has a favourable effect on the spinning performance was described for example in DE 10 2008 026 075 or in the technical article by S. S. Raje et al., which appeared in "Man-Made Textiles in India", p. 173-178, 1996.

For the antioxidative properties, the use of the 2,2,6,6-tetraalkylpiperidinyl radical has proved its worth (so-called HALS compound), as can be applied, for example via 4-amino-2,2,6,6-tetramethylpiperidine (short name triacetonediamine, abbreviation TAD, see e.g. DE 19 854 421 A1) or the additive marketed under the trade name Nylostab-SEED (see e.g. DE 10 2008 026 075 A1 or F. P. La Mantia et al. in "Polymers For Advanced Technologies", 16, 2005, 357-361). Basically, it is possible both to introduce the functional group of the 2,2,6,6-tetraalkylpiperidinyl radical in the form of an additional inert compound or else to bond it to the polymer. The former has the disadvantage that the additive can be washed out over time, the latter has to date been possible only with quasi-monofunctional compounds which act, at the same time, as chain-length controllers but which do not modify the molar mass distribution, such as e.g. with the mentioned 4-amino-2,2,6,6-tetramethylpiperidine.

In order to ensure high melt stability, it is important to minimise the number of reactive chain ends. This reduces the speed of a postcondensation and of a monomer reformation, e.g. during remelting of polyamide 6. The quantity-wise use of chain-length controllers is limited by the technical procedural possibilities and consideration of economic factors.

Since amino end groups are important for good dyeing, as described for example in EP 0 891 491 A1, tertiary amines are introduced into the polymer. These cannot enter into any amide bonding and therefore are maintained for the dyeing, independently of reaction occurrences. In this way, the content of primary amine groups being able to undergo a condensation reaction which are relevant for a monomer reformation are arbitrarily reduced, however, good dyeability remains ensured at the same time.

Since the raw material costs represent the major part of the market price of polyamide, the addition possibilities of additives which are significantly more expensive than the corresponding monomer (caprolactam) are limited. The extra costs produced by additivation must be compensated for by higher performance and a higher-quality material.

Starting herefrom, it was the object of the present invention to provide a universal additive which has both the function of a chain-length controller and that of a thermal stabiliser, acts favourably with respect to dyeing and can narrow the molar mass distribution at the same time.

This object is achieved by the additive, the additive solution, and the polyamide moulding compound described herein. Uses and advantageous developments of the invention are also described.

According to the invention, an additive having at least two functionalities being able to undergo a condensation reaction of the general formula I is provided:

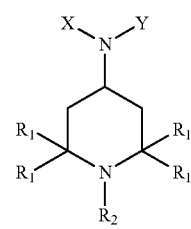

with
$R_1$, independently of each other, H or $C_1$-$C_{12}$ alkyl,
$R_2$=H or $C_1$-$C_{12}$ alkyl and
X and Y, independently of each other, an aliphatic or unsaturated or aromatic carbon framework, linear or branched, with 1 to 12 carbon atoms, X and Y respectively having at least a carboxy-, an amine- or an alcohol functionality.

The additive according to the invention ensures a narrower molar mass distribution compared with a partial or complete stabilisation with monofunctional chain-length controllers. The HALS compound and also the tertiary amine are not bonded to the chain end as previously customary, but incorporated in the chain and hence, provided there are the same technical procedural conditions, no longer reduce the potential to lower the polydispersity. A performance gain in the sphere of high-speed spinning can therefore be expected.

The additive according to the invention makes it possible, for the first time, to be able to fulfil the mentioned requirements for textile polyamide with a single compound. Hence metering stretches and storage tanks can be reduced to a minimum and, at the same time, the number of suppliers upon whom the production is dependent is reduced. The structures are producible on the basis of existing mass chemicals and no extra costs can be expected relative to existing comparable multicomponent formulations. The mentioned structures enable, for the first time, the incorporation of the HALS compound or of the tertiary amine in the polymer chain. To date, only bonding to the chain end via quasi-monofunctional compounds has been possible, which limits the possibilities for modification of the molar mass distribution. Due to the gain in potential of designing the molar mass distribution to be narrower, performance increases in the sphere of high-speed spinning are possible since the melt strength is reduced but the strength in the solidified state is increased.

A preferred additive according to the invention has the general formula II:

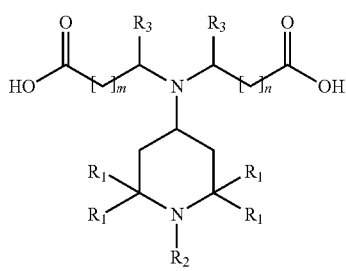

II

There are hereby meant $R_1$ and $R_2$, respectively independently of each other, H or $C_1$-$C_{12}$ alkyl, $R_3$, independently of each other, H or an aliphatic or unsaturated or aromatic carbon framework, linear or branched, with 1 to 12 carbon atom and m and n, respectively independently of each other, 0 to 10, Preferably, at least one of the radicals $R_3$ has a carboxy functionality. In particular, at least one of the radicals $R_3$ is $CH_2COOH$.

A particularly preferred embodiment of the additive according to the invention has the formula III:

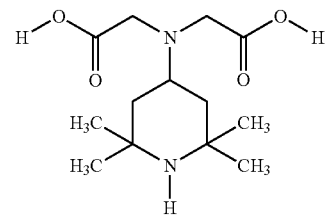

III

According to the invention, an additive solution is likewise provided, which comprises the previously described additive together with caprolactam. Further additives can be contained in this solution.

Preferably, the additive solution can comprise in addition bifunctional carboxylic acids, such as terephthalic acid and/or adipic acid.

According to the invention, a polyamide moulding compound which has an additive is likewise provided, the additive being bonded covalently in the polymer chain via at least two functionalities being able to undergo a condensation reaction.

Preferably, units of general formula IV are incorporated in the polymer chain:

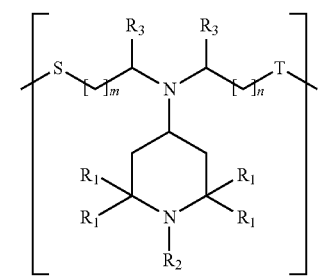

IV with $R_1$ and $R_2$, respectively independently of each other, H or $C_1$-$C_{12}$ alkyl, $R_3$, independently of each other, H or an aliphatic or unsaturated or aromatic carbon framework, linear or branched, with 1 to 12 carbon atoms and S and T, independently of each other, O, NH or COO and m and n, respectively independently of each other, 0 to 10.

A particularly preferred embodiment provides that units of general formula V are incorporated in the polymer chain:

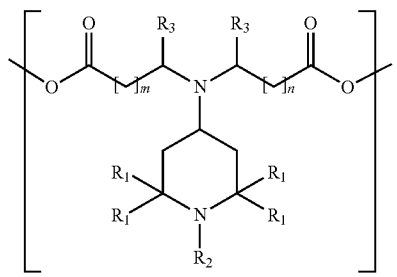

V with $R_1$ and $R_2$, respectively independently of each other, H or $C_1$-$C_{12}$ alkyl, R₃, independently of each other, H or an aliphatic or unsaturated or aromatic carbon framework, linear or branched, with 1 to 12 carbon atoms and m and n, respectively independently of each other, 0 to 10.

For particular preference, units of formula VI are incorporated in the polymer chain:

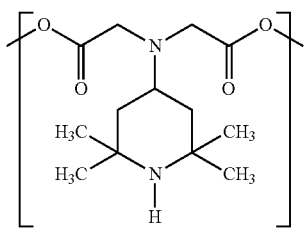

VI

It is thereby preferred that the polyamide moulding compound has a polydispersity in the range of 1.3 to 2.5, in particular 1.5 to 2.0.

The additive according to the invention, as previously described, is used in the production of polycondensates, in particular polyamide moulding compounds, preferably for textile applications.

The subject according to the invention is intended to be explained in more detail with reference to the subsequent Figures and examples without wishing to restrict said subject to the special embodiments shown here.

FIG. 2 shows, by means of a diagram, the relative viscosity as a function of time.

COMPARATIVE EXAMPLE 1 (CE1)

Figure 1:
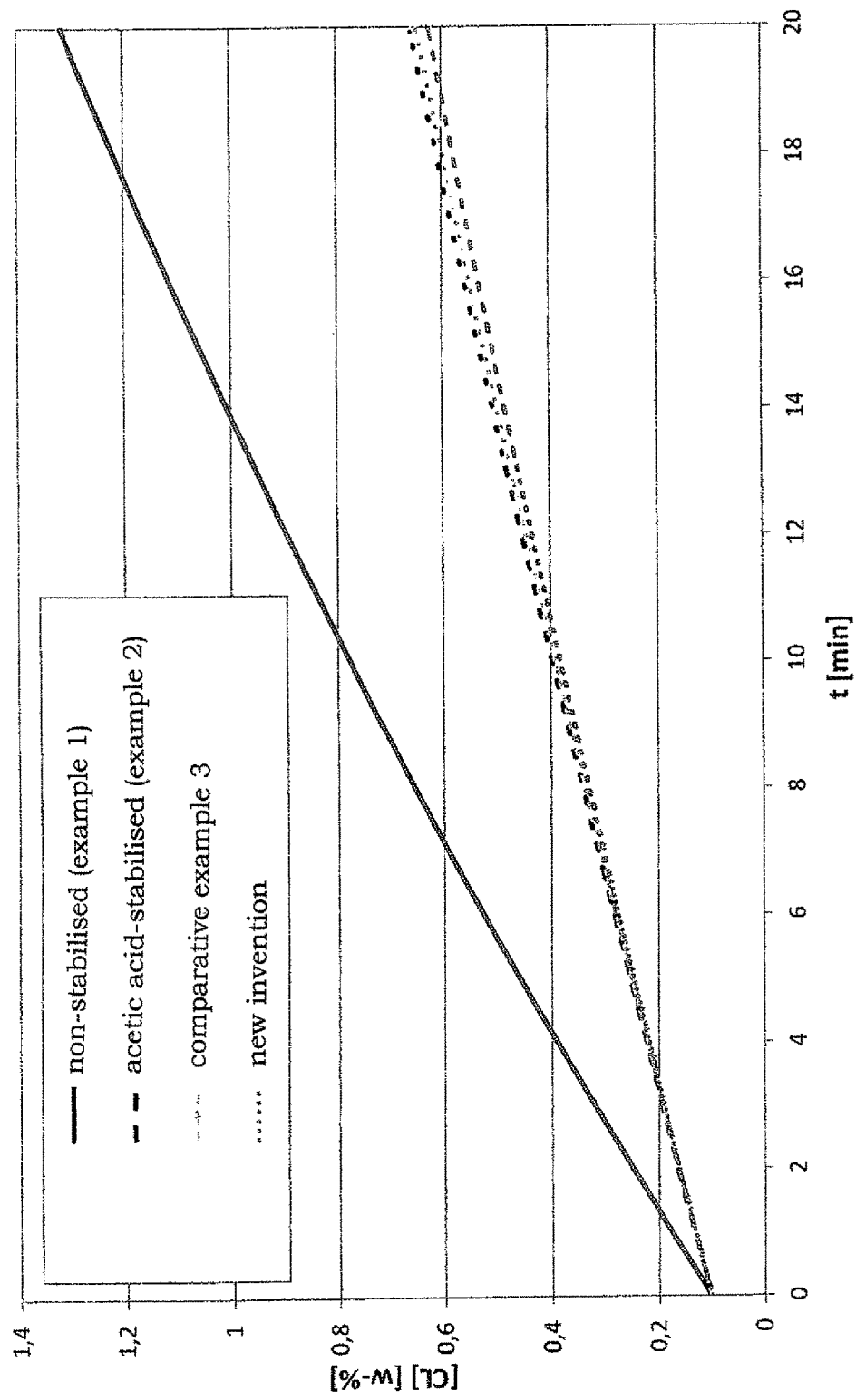
FIG. 1 shows, by means of a diagram, the reformation of caprolactam as a function of time.

Caprolactam is polymerised at a constant water content of 300 mmol/kg (0.54% by weight) at 245° C. until reaching the polycondensation equilibrium. Subsequently, the polymer is granulated and excess caprolactam is extracted with hot water up to 0.1% by weight (8.84 mml/kg). Via drying in the nitrogen flow, subsequently the water content is reduced to 0.05% by weight (27.8 mmol/kg).

COMPARATIVE EXAMPLE 2 (CE2)

Caprolactam and 41.7 mmol/kg of acetic acid are polymerised at a constant water content of 125 mmol/kg (0.225% by weight) at 245° C. until reaching the polycondensation equilibrium. The further processing is effected analogously to comparative example 1.

COMPARATIVE EXAMPLE 3 (CE3)

Caprolactam, 33.4 mmol/kg of terephthalic acid and 17.5 mmol/kg of triacetonediamine are polymerised at a constant water content of 125 mmol/kg (0.225% by weight) at 245° C. until reaching the polycondensation equilibrium. The further processing is effected analogously to comparative example 1.

EXAMPLE 1 (ACCORDING TO THE INVENTION, E1)

Caprolactam, 19.03 mmol/kg of terephthalic acid and 17.5 mmol/kg of compound III are polymerised at a constant water content of 125 mmol/kg (0.225% by weight) at 245° C. until reaching the polycondensation equilibrium. The further processing is effected analogously to comparative example 1.

Table 1 compares the properties of the synthesised polymers of comparative examples 1 to 3 and of example 1 according to the invention. All have the same relative viscosity which can be used as a measure of the processability in the molten state. If the 4 polymers are melted under identical conditions at 260° C. and the reformation of caprolactam and also the change in relative viscosity are followed over time, the results illustrated in FIGS. 1 and 2 are produced. It emerges therefrom that, for a low reformation of caprolactam which acts as plasticiser and hence changes the physical properties and also can lead during spinning to undesired smoke formation, just as for low postcondensation, the use of stabilisers is absolutely necessary. The type of stabiliser is thereby practically irrelevant. For textile applications of the highest requirement, in addition a good anti-oxidative effect, good dyeability and high strength of the polymer are however required. The use of compound III in combination with terephthalic acid (CE1) enables, in contrast to the combination of triacetonediamine and terephthalic acid (CE3), under identical reaction conditions and with the same resistance to weathering conditions (equal concentration of HALS radicals), both a reduction in polydispersity (increased strength in the solidified state) and a higher concentration of amine end groups, which in turn is favourable for dyeing.

TABLE 1

| Sample | rel. viscosity*⁾ | amine end groups [mmol/kg] | carboxyl end groups [mmol/kg] | HALS radical [mmol/kg] | poly-dispersity |
|---|---|---|---|---|---|
| CE1 | 2.37 | 71.41 | 71.41 | — | 2.0 |
| CE2 | 2.37 | 29.74 | 71.44 | — | 2.0 |
| CE3 | 2.37 | 45.12 | 76.92 | 17.5 | 1.71 |
| E1 | 2.37 | 57.28 | 95.34 | 17.5 | 1.65 |

*⁾measured as 1% by weight solution in concentrated sulphuric acid

The invention claimed is:

1. A compound having at least two functionalities being able to undergo a condensation reaction, of general formula II:

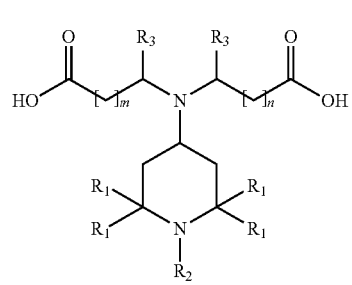

II wherein

R₁ and R₂, respectively independently of each other, are H or $C_1$-$C_{12}$ alkyl, R₃ is independently H or an aliphatic or unsaturated or aromatic carbon framework, linear or branched, with 1 to 12 carbon atoms, wherein at least one of the radicals R₃ has a carboxy-, an amine- or an alcohol functionality; and wherein m and n, respectively independent of each other, are 0 to 10.

2. The compound according to claim 1,
wherein at least one of the radicals $R_3$=$CH_2COOH$.

3. A solution comprising caprolactam and a compound according to claim 1.

4. The solution according to claim 3,
wherein the solution comprises in addition bifunctional carboxylic acids, and mixtures thereof.

5. A method for the production of polycondensates comprising utilizing a compound according to claim 1 in the production of the polycondensates.

6. A method for the production of polyamide moulding compounds comprising utilizing a compound according to claim 1.

\* \* \* \* \*